United States Patent [19]

Seiler et al.

[11] 4,061,537

[45] Dec. 6, 1977

[54] POLYIONIC ISOTONIC SALT SOLUTION

[75] Inventors: Fritz Seiler, Marburg an der Lahn; Andreas Michael Schwarzbeck, Mannheim, both of Germany

[73] Assignee: Behringwerke Aktiengesellschaft, Marburg an der Lahn, Germany

[21] Appl. No.: 705,816

[22] Filed: July 16, 1976

[30] Foreign Application Priority Data

July 18, 1975 Germany .............................. 2532183

[51] Int. Cl.$^2$ .......................... C12B 3/00; C12K 1/10
[52] U.S. Cl. ...................................... 195/1.7; 195/1.8; 195/100; 195/102
[58] Field of Search .................. 195/1.7, 1.8, 100, 102

[56] References Cited

U.S. PATENT DOCUMENTS

| 3,444,039 | 5/1969 | Rajamannan | 195/1.7 |
| 3,551,290 | 12/1970 | Kuwahara et al. | 195/1.7 |
| 3,862,002 | 1/1975 | Sanders | 195/1.7 |

*Primary Examiner*—Sam Rosen
*Attorney, Agent, or Firm*—Curtis, Morris & Safford

[57] ABSTRACT

Polyionic isotonic salt solution consisting of physiologically tolerable cations and anions and, optionally, colloids and a variety of substances known as additives to perfusion solutions, comprising $\geq$ 80 mval/l potassium, $\geq$ 1.7 mval/l of magnesium and, as anions, chloride, sulfate, phosphate and anions of organic aliphatic fatty acids or hydroxylic acids in a concentration of 90–160 mval/l in total, whereby the chloride ions are contained in physiological concentration of 100 mval/l at most.

2 Claims, No Drawings

POLYIONIC ISOTONIC SALT SOLUTION

The present invention relates to a polyionic isotonic salt solution.

This polyionic isotonic salt solution is particularly suitable for the preservation of erythrocytes and for preserving transplant kidneys through perfusion. In addition it is valuable for the stabilization of the viability of various microorganisms, especially of virus particles.

Aqueous isotonic salt solutions have been known for a long time. They are used in clinics and biological laboratories when cells or tissues or organs are to be treated under conditions that relate closely to the osmotic conditions of the serum.

In this respect, the simplest isotonic solution is the well-known physiological sodium chloride solution containing about 9 g of NaCl per 1,000 g of water. Further developments led to buffered solutions and to Ringer's solution. Solutions of this type and similar ones (Tyrode's solution, Ringer-Locke's solution, and others, and solutions including additives of magnesium and phosphate and other ions), are necessary for experiments under physiological conditions, i.e. the perfusion of isolated organs, or the preparation and preserving of cells.

The clinical value of these solutions, the composition of which aims at imitating the salt composition of the blood serum, is not yet clearly defined, because the role that calcium, phosphate and magnesium ions play in connection with parenteral water and electrolyte replacement therapy has not yet been made sufficiently clear and the administration of these ions by means of the various available infusion fluids is as yet still the subject of practical evaluation and of theoretical considerations.

Various isotonic solutions to be mentioned in this context, especially when used for the perfusion of transplanted kidneys, gave moderate or unsatisfactory results. Therefore, perfusion solutions have been developed in the past essentially on the basis of plasma proteins, especially of albumin. Plasma proteins, such as albumin, are not available in any desired quantity and they are also relatively expensive.

It was therefore desirable to find a solution capable of replacing to a large extent the solutions containing plasma proteins.

A solution having the following characteristics met these requirements:

The total cation content of sodium, potassium, magnesium and calcium corresponds to the mean content of the total sum of cations of a normal human serum. It is 150–160 mval/l (meq/l), but the content may be raised to 210 mval/l to obtain a desired hyperosmolarity. Typical characteristics of this solution are its content of potassium ions in an amount of >80 mval/l preferably 120–130 mval/l and their content of magnesium ions of >1.7 mval/l preferably 6–30 mval/l whereby it is possible to replace the content of calcium in the serum to a large extent. The content of sodium in the solution corresponds to the difference between the sum of the stated cations and the sum of the cation concentrations contained in the serum, or at most to the difference between the sum of mval of the stated cations and the total content of cations corresponding to 210 mval/l The present solution is further characterized in that the chloride which is the prevailing anion in the serum and is contained in a concentration of about 100 mval/l is replaced by anions, such as phosphate, sulfate and the anions of organic, physiologically tolerable aliphatic fatty acids; for example lactic acid, caprylic acid, lauric acid or myristic acid. The content of chloride ions in the present solution is 100 mval/l at most, preferably 30–70 mval/l. The present solution is also characterized by a content of substances having colloidosmotic effect, for example proteins, such as albumin or such as gelatine derivatives in a concentration of 0.5–5% by weight, preferably of 2–3% by weight, which had been obtained by decomposition of gelatine followed by reaction with hexamethylene diisocyanate according to German Pat. No. 1118732. It is advantageous to add a low molecular weight carbohydrate to the solution, for example glucose, in a concentration of 3–10 g, preferably 7–8 g/l, and sometimes mannitol, xylitol or inulin in a concentration of up to 3–20 g, preferably 4–10 g/l. Moreover, physiological products of the intermediary metabolism, such as succinate, α-ketoglutarate or oxal acetate may be added.

Generally, the preparation of the aqueous salt solution prepared and composed as mentioned before results in a pH value ranging from 6.9–7.4, which if necessary, can be adjusted by means of acid or alkaline solution.

Depending on the intended application of the solution, for example organ perfusion or the preservation of erythrocytes, further additives are added to the solution, for example heparin in a quantity of up to 15 IU/ml, an antibiotic, for example penicillin in a quantity of up to 200 IU/ml, insulin in an quantity of up to 0.25 IU/ml. If desired, vasoactive substances, for example α-receptor blockers, may be added, especially to the perfusion solution.

The process for the preparation of the solution comprises the dissolution of the substances, which have to be weighed exactly, in distilled, sterile and preferably pyrogen-depleted water. The fatty acids are advantageously used as sodium or potassium salts.

Several representative examples of compositions of solutions in accordance with the invention are listed:

| Solution No. 1 | | |
|---|---|---|
| $KH_2PO_4$ anhydride | 1.3610 g | 10 mval $K^+$ |
| $K_2HPO_4$ anhydride | 8.5714 g | 100 mval $K^+$ |
| KCl | 1.1108 g | 15 mval $K^+/Cl^-$ |
| Na lactate (50 %) | 1.6814 g | 7.5 mval $Na^+$ |
| NaCl | 1.1690 g | 20 mval $Na^+/Cl^+$ |
| glucose | 7.8470 g | |
| modified collagen decomposition product (10 % in solution, having a low salt content) | 300 ml | |
| $MgSO_4 . 7 H_2O$ | 1.8496 g | 15 mval $Mg^{++}$ |
| phenol red (20ml, 0.1 %) | 0.0200 g | |
| heparin (100 IU/mg) | 5,000 IU | |
| penicillin | 100,000 IU | |
| swine insulin | 125 IU | |
| all substances dissolved in distilled water, | | |
| To make | 1,000 ml | |
| pH 7.28 | | |
| 274 mOsm | | |
| Total content of the solution: 125 mval $K^+$ 27.5 mval $Na^+$ 15 mval $Mg^{++}$ 35 mval $Cl^-$ | | |

Instead of a modified collagen decomposition product, for example human albumin or polyvinyl pyrrolidone can be used in a quantity of, for example 30 g per 1,000 ml.

Solution No. 2:

| | | |
|---|---|---|
| KH$_2$PO$_4$ | 1.361 g | 10 mval K$^+$ |
| K$_2$HPO$_4$ | 8.5714 g | 100 mval K$^+$ |
| KCl | 1,1108 g | 15 mval K$^+$ |
| NaCl | 1.1690 g | 20 mval Na$^+$ |
| Na lactate (50 %) | 1.6814 g | 7.5 mval Na$^+$ |
| MgSO$_4$ . 7 H$_2$O | 3.6991 g | 7.5 mval Mg$^{++}$ |
| glucose | 7.847 g | |
| human albumin | 30 g/1000 ml | |
| phenol red (20 ml, 0.1 %) | 0.0200 g | |
| heparin (100 IU/mg) | 5,000 IU | |
| penicillin | 100,000 IU | |
| swine insulin | 125 IU | |
| all substances dissolved in distilled water | | |
| To make | 1,000 ml | |
| pH 7.2 – 7.3 | | |
| 280 – 290 mOsm | | |
| Total content of the solution: | | |
| | Cations: | Anions: |
| | 125 mval K$^+$ | 60 mval phosphate |
| | 27.5 mval Na$^+$ | 35 mval Cl$^-$ |
| | 7.5 mval Mg$^{++}$ | 7.5 mval lactate |

Solution No. 3:

| | | |
|---|---|---|
| KH$_2$PO$_4$ | 1.361 g | 10 mval K$^+$ |
| K$_2$HPO$_4$ | 8.5714 g | 100 mval K$^+$ |
| KCl | 1.4914 g | 20 mval K$^+$ |
| NaCl | 2.1916 g | 37.5 mval Na$^+$ |
| Na-lactate (50 %) | 1.6814 g | 7.5 mval Na$^+$ |
| MgSO$_4$ . 7 H$_2$O | 3.6991 g | 30 mval Mg$^{++}$ |
| D(–)-mannitol | 4.0000 g | |
| glucose 7.8470 g | | |
| human albumin | 30.0000 g | |
| phenol red (20 ml; 0,1 %) | 0.0200 g | |
| heparin | 5000 IU | |
| penicillin | 100 000 IU | |
| all substances dissolved in distilled water | | |
| To make | 1,000 ml | |
| pH 7.22 | | |
| 345 mOsm | | |
| Total content of the solution: | | |
| | cations: | anions: |
| | 130 mval K$^+$ | 60 mval phosphate |
| | 45 mval Na$^+$ | 57.5 mval Cl$^-$ |
| | 30 mval Mg$^{++}$ | 7.5 mval lactate |
| | | 30 mval SO$_4^{--}$ |

Solution No. 4:

| | | |
|---|---|---|
| KH$_2$PO$_4$ | 1.3610 g | 10 mval K$^+$ |
| K$_2$HPO$_4$ | 8.5714 g | 100 mval K$^+$ |
| KCl | 1.4914 g | 20 mval K$^+$ |
| NaCl | 2.6299 g | 45 mval Na$^+$ |
| Na lactate (50 %) | 3.3628 g | 15 mval Na$^+$ |
| MgSO$_4$ . 7 H$_2$O | 1.8495 g | 15 mval Mg$^{++}$ |
| glucose | 7.8470 g | |
| mannitol | 10.0000 g | |
| human albumin | 30.0000 g | |
| phenol red (20 ml, 0.1 %) | 0.0200 g | |
| heparin | 5000 IU | |
| penicillin | 100 000 IU | |
| caprylic acid | 0.2307 g | 1600 μmol |
| lauric acid | 0.1602 g | 800 μmol |
| myristic acid | 0.0913 g | 400 μmol |
| all substances dissolved in distilled water | | |
| To make | 1,000 ml | |
| pH 7.15 | | |
| conductivity: | 14.2 mS | |
| Total content of the solution: | | |
| | cations: | anions: |
| | 130 mval K$^+$ | 60 mval phosphate |
| | 60 mval Na$^+$ | 65 mval Cl$^-$ |
| | 15 mval Mg$^{++}$ | 15 mval lactate |
| | | 15 mval SO$_4^{--}$ |

The aforementioned examples of solutions exhibited particular advantageous properties when used selectively. Thus solution No. 1 considerably improved the stability or erythrocytes on storage: A suspension of human or animal erythrocytes in solution No. 1 showed a considerably reduced tendency towards spontaneous hemolysis and a distinctly better resistance to osmosis.

Use of solution No. 1 is advantageous as a preserving medium of the viability of microorganisms. Especially virus particles retain their viability even when freeze dried therein.

During transplantation experiments with perfused dog kidneys good results were obtained when solution No. 3, solution No. 4 or a mixture of these solutions in the ratio 1 : 1 were used. A measure for these results are a reduced weight increase of the perfused kidneys, a high discharge of urine and a good organ function after re-implantation of the kidneys perfused with the solutions in the extracorporeal circulation over a prolonged period of time.

What is claimed is:

1. In a polyionic aqueous salt solution adaptable to the preservation of erythrocytes and of organs for transplantation and to maintaining the viability of microorganisms, said solution comprising physiologically tolerable cations and anions, the improvement wherein said solution comprises potassium ions at a concentration equal to or greater than 80 mval per liter, comprises magnesium ions at a concentration equal to or greater than 1.7 mval per liter, and which comprises, as anions, a total concentration between 90 mval per liter and 160 mval per liter of chloride, sulfate, phosphate, and anions of an organic aliphatic fatty acid or of an aliphatic hydroxy acid, the concentration of chloride anions being at most 100 mval per liter.

2. A solution as in claim 1 which additionally comprises a colloid.

* * * * *